United States Patent [19]
Mizuide et al.

[11] Patent Number: 6,008,300
[45] Date of Patent: Dec. 28, 1999

[54] BISPHENOL COMPOUND AND FLUORINE-CONTAINING ELASTOMER COMPOSITION CONTAINING THE SAME

[75] Inventors: Fumiyo Mizuide; Satoru Saito, both of Kitaibaraki; Haruyoshi Tatsu, Hitachi, all of Japan

[73] Assignee: Nippon Mektron Limited, Tokyo, Japan

[21] Appl. No.: 08/838,492

[22] Filed: Apr. 7, 1997

[30] Foreign Application Priority Data

Jul. 31, 1996 [JP] Japan .................................. 8-217984

[51] Int. Cl.$^6$ ...................................................... C08F 8/40
[52] U.S. Cl. .......................... 525/274; 524/139; 525/276; 525/326.3; 525/326.4; 525/340
[58] Field of Search ............................ 524/139; 525/274, 525/276, 326.3, 326.4, 340

[56] References Cited

U.S. PATENT DOCUMENTS

| | | |
|---|---|---|
| 3,816,143 | 6/1974 | Anderson et al. ................. 524/139 |
| 4,496,682 | 1/1985 | Schmiegel . |
| 4,868,234 | 9/1989 | Tabb et al. . |
| 4,882,390 | 11/1989 | Grootaert et al. . |
| 4,912,171 | 3/1990 | Grootaert et al. . |
| 4,925,892 | 5/1990 | Tabb et al. . |
| 5,262,490 | 11/1993 | Kolb et al. . |
| 5,478,902 | 12/1995 | Yamamoto et al. .................. 526/247 |

*Primary Examiner*—Bernard Lipman
*Attorney, Agent, or Firm*—Kenyon & Kenyon

[57] ABSTRACT

A bisphenol compound represented by the following general formula:

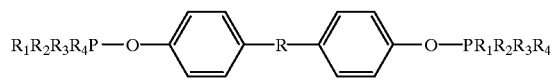

where R is an alkylene group having 1 to 5 carbon atoms, an alkylidene group having 1 to 5 carbon atoms, a perfluoroalkylene group having 1 to 5 carbon atoms, a perfluoroalkylidene group having 1 to 5 carbon atoms, a $SO_2$ group or an O group; and $R_1$, $R_2$, $R_3$ and $R_4$ are the same or different alkyl groups, alkenyl groups, aryl groups, alkylaryl groups or aralkyl groups, each having 1 to 25 carbon atoms, can give vulcanization products having a good resistance to hot water, when used as a cross-linking agent for terpolymers of tetrafluoroethylene/perfluoro (alkyl vinyl ether)/ethylenically unsaturated cure site monomer.

7 Claims, No Drawings

BISPHENOL COMPOUND AND FLUORINE-CONTAINING ELASTOMER COMPOSITION CONTAINING THE SAME

BACKGROUND OF THE INVENTION

1. Field of the Invention

The present invention relates to a novel bisphenol compound and a fluorine-containing elastomer composition containing the same, and more particularly to a novel bisphenol compound effectively applicable as a cross-linking agent for fluorine-containing elastomers and a fluorine-containing elastomer composition containing the same.

2. Description of Related Art

The present applicant found earlier that when 1,1,3,3,3-pentafluoropropene was copolymerized with tetrafluoroethylene and perfluoro(methyl vinyl ether) and the resulting terpolymer was vulcanized with the aid of a dialkali metal salt of bisphenol type compound. vulcanization products having a low compression set could be obtained (see U.S. Pat. No. 5,478,902).

As a result of further studies of the composition, it was found that when the vulcanization molding articles were used as seals for oil well plants, etc., the articles were not satisfactory yet with respect to durability to hot water.

SUMMARY OF THE INVENTION

An object of the present invention is to provide a novel bisphenol compound capable of giving vulcanization products having a good resistance to hot water, when used as a cross-linking agent for terpolymer elastomers of tetrafluoroethylene/perfluoro(alkyl vinyl ether)/ethylenically unsaturated cure site monomer.

A novel bisphenol compound according to the present invention can be represented by the following general formula:

$$R_1R_2R_3R_4P-O-\phi-R-\phi-O-PR_1R_2R_3R_4$$

where R is an alkylene group having 1 to 5 carbon atoms, an alkylidene group having 1 to 5 carbon atoms, a perfluoroalkylene group having 1 to 5 carbon atoms, a perfluoroalkylidene group having 1 to 5 carbon atoms, a $SO_2$ group or an O group; and $R_1$, $R_2$, $R_3$ and $R_4$ are the same or different alkyl groups, alkenyl groups, aryl groups, alkylaryl groups or aralkyl groups, each having 1 to 25 carbon atoms.

DETAILED DESCRIPTION OF THE INVENTION

The present novel bisphenol compound can be produced by reaction of one parts by mole of a bisphenol compound represented by the following general formula:

$$HO-\phi-R-\phi-OH$$

with 2 parts by mole of a quaternary phosphonium halide represented by the following general formula:

$$PR_1R_2R_3R_4X.$$

Bisphenol compounds whose R group is:

$$-\underset{\underset{CF_3}{|}}{\overset{\overset{CF_3}{|}}{C}}-,\quad -\underset{\underset{CH_3}{|}}{\overset{\overset{CH_3}{|}}{C}}-,\quad -CH_2-,$$

$$-O-,\quad -SO_2-, \text{ etc.}$$

are used as starting bisphenol compounds. Preferably, the following bisphenol compounds are used in the present invention:

$$HO-\phi-\underset{\underset{CF_3}{|}}{\overset{\overset{CF_3}{|}}{C}}-\phi-OH$$

and $$HO-\phi-\underset{\underset{CH_3}{|}}{\overset{\overset{CH_3}{|}}{C}}-\phi-OH$$

Quaternary phosphonium halide represented by the following general formula is used for the reaction with the bisphenol compound in a ratio of the former to the latter of 2:1 by mole:

$$(R_1R_2R_3R_4P)^+X^-$$

where $R_1$, $R_2$, $R_3$ and $R_4$ are the same or different alkyl groups, alkenyl groups, alkoxy groups, aryl groups, alkylaryl groups or aralkyl groups, each having 1 to 25 carbon atoms; and $X^-$ is $Cl^-$ or $Br^-$.

Specifically, the quaternary phosphonium salt for use in the present invention includes, for example, tetraphenylphosphonium chloride, triphenylbenzylphosphonium chloride, triphenylbenzylphosphonium bromide, triphenylmethoxymethylphosphonium chloride, triphenylmethylcarbonylmethylphosphonium chloride, triphenylethoxycarbonylmethylphosphonium chloride, trioctylbenzylphosphonium chloride, trioctylmethylphosphonium bromide, tetraethylphosphonium chloride, tetrapropylphosphonium chloride, tetrabutylphosphonium chloride, tetraoctylphosphonium chloride, tetravinylphosphonium chloride, tetraallylphosphonium chloride, tetrabenzylphosphonium chloride, cetyldimethylbenzylphosphonium chloride, etc.

Reaction therebetween can be carried out at a reaction temperature of room temperature to about 50° C. by dropwise adding a solution of quaternary phosphonium halide in methanol to a solution of dialkali metal salt, typically, disodium salt, dipotassium salt, monosodium-monopotassium salt, of starting bisphenol compound in a polar solvent such as methanol, ethanol, acetone, etc. The desired bisphenol compound can be obtained by removing the alkali metal halide precipitates and the reaction solvents from the resulting reaction mixture.

The thus obtained novel bisphenol compound can be used as a cross-linking agent for terpolymer elastomers of tetrafluoroethylene/perfluoro(alkyl vinyl ether)/ethylenically unsaturated cure site monomer. Generally, perfluoro(methyl vinyl ether) [FMVE] can be used for the perfluoro(alkyl vinyl ether) as the terpolymer component. Ethylenically unsaturated compounds represented by the following general formula:

$$R_5CH=CR_6R_7$$

where $R_5$ and $R_6$ each H an F, and $R_7$ is H, F, an alkyl group or a perfluoroalkyl group, each having 1 to 5 carbon atoms, can be used as the ethylenically unsaturated cure site monomer, and include, for example, $CH_2=CH_2$, $CH_2=CHF$, $CH_2=CF_2$, $CHF=CF_2$, $CH_2=CFCF_3$, $CF_2=CH_2CF_3$, $CH_2=CHCF_2CF_2CF_3$, etc. Preferable are 1,1,3,3,3-pentafluoropropene [5FP], trifluoroethylene and vinylidene fluoride.

Terpolymer elastomers obtained by copolymerization of these monomers have such a copolymer composition as about 45 to about 80% by mole, preferably about 47 to about 65% by mole, of tetrafluoroethylene [TFE], about 20 to about 50% by mole, preferably about 35 to about 50% by mole, of perfluoro(alkyl vinyl ether) and about 0.1 to about 5% by mole, preferably about 0.1 to about 3% by mole, of a ethylenically unsaturated cure site monomer, sum total being 100% by mole, and have such a viscosity characteristic as a ηsp/c value of about 0.3 to about 5 dl/g, as determined at 35° C. in Fluorinert FC-77 [trade-mark of an inert liquid consisting mainly of perfluoro(2-butyltetrahydrofuran), made by Sumitomo 3M Co., Ltd., Japan]. The terpolymer can be further copolymerized with other vinyl monomer or olefinic monomer to such an extent as not to inhibit the object of the present invention, generally not more than about 20% by mole, preferably not more than about 10% by mole.

The present novel bisphenol compound acting as a cross-linking agent for such terpolymer elastomers can be used in an amount of about 0.5 to about 10 parts by weight, preferably about 1 to about 5 parts by weight, per 100 parts by weight of the terpolymer elastomer. Below about 0.5 parts by weight, the desired effect of the present invention, i.e. improvement of resistance to hot water of the vulcanization products, cannot be obtained, and mechanical properties of the vulcanization products will be lowered. Whereas above about 10 parts by weight, the resistance to organic solvents of the vulcanization products will be lowered.

Dialkali metal salts of bisphenol type compounds (the same bisphenol type compounds as the starting compounds represented by the foregoing general formula, as used in the present invention) in addition to the present novel bisphenol compound acting as a cross-linking agent, preferably, disodium salts, dipotassium salts, monosodium-monopotassium salts, etc. of bisphenol AF and bisphenol A, capable of improving compression set, can be used in the vulcanization in an amount of about 0.5 to about 10 parts by weight, preferably about 1 to about 6 parts by weight, per 100 parts by weight of the terpolymer. Furthermore, a filler such as carbon black, silica, etc., a rein-forcing agent, an acid acceptor such as oxides, hydroxides, etc. of divalent metals, and other necessary additives can be properly used upon mixing.

The present fluorine-containing elastomer composition can be prepared by the ordinary mixing method using an open roll, a Bambury mixer, etc., and the thus prepared composition can be vulcanized by press vulcanization (primary vulcanization) at about 100 to about 250° C. for about 1 to about 120 minutes and then by oven vulcanization (secondary vulcanization) at about 150 to about 300° C. for 0 to 50 hours.

When the present novel bisphenol compound is used as a cross-linking agent for terpolymer elastomers of tetrafluoroethylene/perfluoro(alkyl vinyl ether)/ ethylenically unsaturated cure site monomer, vulcanization products having a distinguished resistance to hot water can be obtained. Thus, the terpolymer elastomers containing the present novel bisphenol compound can be effectively used in such applications as seals for oil well plants.

PREFERRED EMBODIMENTS OF THE INVENTION

The present invention will be described in detail below, referring to Examples and Comparative Examples.

EXAMPLE 1

20 g (59 m moles) of bisphenol AF was dissolved in 500 ml of methanol and then flushed with a nitrogen gas for 30 minutes. Then, a two-fold molar amount of sodium methoxide was dropwise added thereto as 200 ml of methanol solution. After stirring for one hour, a solution of 51 g (131 m moles) of benzyltriphenylphosphonium chloride dissolved in 500 ml of methanol was dropwise added thereto with stirring, and then stirring was continued for further 20 minutes. A series of these operations was all carried out at room temperature. Then, methanol was removed from the reaction mixture by distillation under reduced pressure, a yellowish viscous material remained as residues.

One liter of ion-exchanged water was added to the residues, and the mixture was stirred at 60° C. for 2 hours, then cooled to 5° C. and left standing for one hour. The aqueous layer was removed therefrom by decantation, whereby a water-containing, viscous liquid was obtained. The liquid was dried at 40° C. under reduced pressure overnight, whereby 52 g of brownish solid was obtained (yield: 78%). The solid was highly hygroscopic and preserved in a $P_2O_5$ desiccator. The solid had the following elemental analysis and chemical formula:

Elemental analysis

Calculated: C 74.71%, H 5.06%, P 6.03%, O 3.11%, F 11.09%

Found: C 74.2%, H 5.3%, P 6.0%, O 3.2% F 11.3%

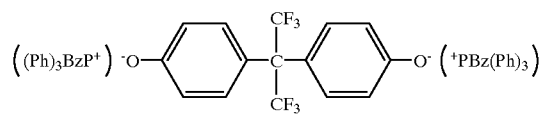

Bz: Benzyl group
Ph: Phenyl group

EXAMPLE 2

33.7 g (0.1 mole) of bisphenol AF was dissolved in 125 ml of methanol and flushed with a nitrogen gas for 30 minutes. Then, a two-fold molar amount of sodium methoxide in methanol was dropwise added thereto as a methanol solution. After stirring for one hour, a solution containing 67.8 g (0.2 moles) of tetrabutylphosphonium bromide in 250 ml of methanol was dropwise added thereto with stirring, and then the mixture was left standing for 30 minutes. A series of these operations was all carried out at room temperature. The reaction mixture was concentrated to a half volume by an evaporator and left standing for 1 to 2 days, whereby crystals were precipitated. Crystal portions and liquid portions were separated from each other by filtration under reduced pressure, and the filtrate was poured into a large amount of acetone. The precipitated crystals were filtrated off. The resulting filtrate was further concentrated to the limit by an evaporator and dried under reduced pressure, whereby 82.1 g of the desired crystal was obtained (yield: 97.3%).

The thus obtained crystalline product was analyzed. It was found that the product had the following chemical formula and elemental analysis:

$^1$H—NMR:

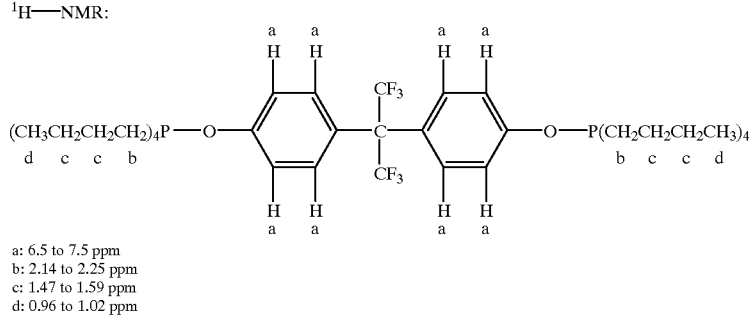

a: 6.5 to 7.5 ppm
b: 2.14 to 2.25 ppm
c: 1.47 to 1.59 ppm
d: 0.96 to 1.02 ppm

Elemental analysis
Calculated: C 66.2%, H 9.4%, P 7.3%, O 3.8%, F 13.4%
Found: C 66.8%, H 9.7%, P 7.2%, O 3.8%, F 12.4%

EXAMPLE 3

The following components were added to 100 parts by weight of terpolymer elastomer of TFE-FMVE-5FP in a molar ratio of 63.6: 35.4: 1.0, which had a ηsp/c value of 0.45 dl/g:

|  | Parts by weight |
| --- | --- |
| MT carbon black | 15 |
| Product of Example 1 | 3 |
| Dipotassium salt of bisphenol AF | 2 |
| Zinc oxide | 4 |

The mixture was kneaded in a roll mill, and the resulting kneaded product was subjected to press vulcanization (primary vulcanization) at 180° C. for 30 minutes and then to oven vulcanization (secondary vulcanization) in a nitrogen atmosphere according to the following schedule:
Holding at 90° C. for 4 hours
Temperature elevation from 90 C. to 204°C. over 6 hours
Holding at 204° C. for 18 hours
Temperature elevation from 204° C. to 288° C. V over 6 hours
Holding at 288° C. for 18 hours
The resulting vulcanization product was subjected to determination of physical properties according to DIN53504 and 53505, resistance to hot water (percent volume reduction by dipping in pressurized hot water at 200° C. for 7 hours), and compression set according to ASTM D-395, Method B (P-24 O -ring at 200° C. for 70 hours).

EXAMPLE 4

In Example 3, the same amount of lead oxide (PbO) was used in place of zinc oxide.

EXAMPLE 5

In Example 3, the amount of MT carbon black was changed to 25 parts by weight, and 10 parts by weight of perfluoropolyether {Aflunox 400, trademark of a product Rf[CF(CF$_3$)CF$_2$ O]nRf made by Nippon Mektron, Ltd., Japan} was further used as a processability-improving agent.

EXAMPLE 6

In Example 3, 13 parts by weight of SAF carbon black was used in place of MT carbon black, and 10 parts by weight of perfluoropolyether (Aflunox 400) was further used.

EXAMPLE 7

In Example 3, the same amount of lead oxide (PbO) was used in place of zinc oxide; the amount of MT carbon black was changed to 25 parts by weight; and 10 parts by weight of perfluoropolyether (Aflunox 400) was further used.

EXAMPLE 8

In Example 3, the same amount of lead oxide (PbO) was used in place of zinc oxide; 13 parts by weight of SAF carbon black was used in place of MT carbon black; and 10 parts by weight of perfluoropolyether (Aflunox 400) was further used.

Comparative Example 1

|  | Parts by weight |
| --- | --- |
| Terpolymer of TFE-FMVE-5FP of Ex. 3 | 100 |
| MT carbon black | 25 |
| Dipotassium salt of bisphenol AF | 3 |
| Zinc oxide | 4 |
| Dicyclohexyl 18-Crownether-6 | 0.5 |

The foregoing components were kneaded, vulcanized and subjected to determination in the same manner as in Example 3.

Comparative Example 2

In Comparative Example 1, the same amount of lead oxide (PbO) was used in place of zinc oxide.

Comparative Example 3

In Comparative Example 1, no zinc oxide was used at all.

EXAMPLE 9

In Example 3, the same amount of the product of Example 2 was used in place of the product of Example 1.

EXAMPLE 10

In Example 5, the same amount of the product of Example 2 was used in place of the product of Example 1.

EXAMPLE 11

In Example 7, the same amount of the product of Example 2 was used in place of the product of Example 1.

Results of determinations in the foregoing Examples 3 to 11 and Comparative Examples 1 to 3 are given in the following Table.

TABLE

|  | Hardness (Shore A) | Tensile stength (MPa) | 100% Modulus (MPa) | Elongation (%) | Resistance to hot water (Δ vol %) | Compression set (%) |
|---|---|---|---|---|---|---|
| Ex. 3 | 73 | 16.1 | 5.1 | 240 | 84.0 | 40 |
| Ex. 4 | 73 | 16.0 | 5.7 | 190 | 86.5 | 30 |
| Ex. 5 | 72 | 13.1 | 4.6 | 230 | 100.3 | 44 |
| Ex. 6 | 73 | 14.9 | 4.4 | 250 | 113.4 | 58 |
| Ex. 7 | 73 | 16.9 | 5.9 | 210 | 67.3 | 31 |
| Ex. 8 | 75 | 17.8 | 6.0 | 210 | 55.0 | 31 |
| Com. Ex. 1 | 67 | 13.6 | 3.8 | 220 | 114.4 | 31 |
| Com. Ex. 2 | 67 | 13.5 | 4.3 | 200 | 139.3 | 32 |
| Com. Ex. 3 | 65 | 10.9 | 3.1 | 230 | 171.7 | 42 |
| Ex. 9 | 78 | 14.8 | 7.1 | 210 | 87.8 | 35 |
| Ex. 10 | 77 | 11.7 | 6.5 | 210 | 78.6 | 38 |
| Ex. 11 | 76 | 12.9 | 7.4 | 180 | 115.5 | 35 |

What is claimed is:

1. A fluorine-containing elastomer composition which comprises a terpolymer elastomer of tetrafluoroethylene/perfluoro(alkyl vinyl ether)/ethylenically unsaturated cure site monomer and a novel bisphenol compound represented by the following general formula:

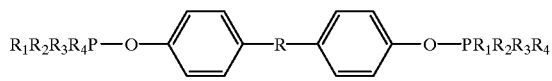

where R is an alkylene group having 1 to 5 carbon atoms, an alkylidene group having 1 to 5 carbon atoms, a perfluoroalkylene group having 1 to 5 carbon atoms, a perfluoroalkylidene group having 1 to 5 carbon atoms, a $SO_2$ group or an O group; and $R_1$, $R_2$, $R_3$ and $R_4$ are the same or different alkyl groups, alkenyl groups, aryl groups, alkylaryl groups or aralkyl groups, each having 1 to 25 carbon atoms.

2. A fluorine-containing elastomer composition according to claim 1, wherein the perfluoro(alkyl vinyl ether) is perfluoro(methyl vinyl ether).

3. A fluorine-containing elastomer composition according to claim 1, wherein the ethylenically unsaturated cure site monomer of the terpolymer elastomer is represented by the following general formula:

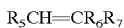

where $R_5$ and $R_6$ each are H or F, and $R_7$ is H, F, an alkyl group or a perfluoroalkyl group, each having 1 to 5 carbon atoms.

4. A fluorine-containing elastomer composition according to claim 3, wherein the ethylenically unsaturated cure site monomer is 1,1,3,3,3-pentafluoropropene, trifluoroethylene or vinylidene fluoride.

5. A fluorine-containing elastomer composition according to claim 1, wherein about 0.5 to about 10 parts by weight of the novel bisphenol compound is used per 100 parts by weight of the terpolymer elastomer.

6. A fluorine-containing elastomer composition according to claim 1, wherein a dialkali metal salt of a bisphenol type compound represented by the following general formula:

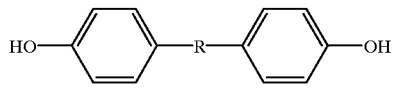

where R is an alkylene group having 1 to 5 carbon atoms, an alkylidene group having 1 to 5 carbon atoms, a perfluoroalkylene group having 1 to 5 carbon atoms, a perfluoroalkylidene group having 1 to 5 carbon atoms, a $SO_2$ group or an O group, is used together with the novel bisphenol compound.

7. A fluorine-containing elastomer composition according to claim 6, wherein about 0.5 to about 10 parts by weight of the dialkali metal salt of a bisphenol type compound is used per 100 parts by weight of the terpolymer elastomer.

* * * * *

UNITED STATES PATENT AND TRADEMARK OFFICE
CERTIFICATE OF CORRECTION

PATENT NO. : 6,008,300
DATED : December 28, 1999
INVENTOR(S) : Mizuide et al.

It is certified that error appears in the above-identified patent and that said Letters Patent is hereby corrected as shown below:

Column 5,
Line 42, after "288° C." delete "V";

Column 6,
After line 39 ("Dicclohexyl 18..."), and before line 40 ("The foregoing components were kneaded..."), insert the following line to "Comparative Example 1":
-- Perfluoropolyether (Aflunox 400)    20 --.

Signed and Sealed this

Eleventh Day of December, 2001

Attest:

NICHOLAS P. GODICI
Attesting Officer   Acting Director of the United States Patent and Trademark Office